(12) United States Patent
Nord et al.

(10) Patent No.: US 8,009,803 B2
(45) Date of Patent: Aug. 30, 2011

(54) TREATMENT PLAN OPTIMIZATION METHOD FOR RADIOSURGERY

(75) Inventors: Janne Ilmari Nord, Espoo (FI); Juha Kauppinen, Espoo (FI); Ramin Baghaie, Espoo (FI); Jukka Suominen, Espoo (FI)

(73) Assignee: Varian Medical Systems International AG, Zug (CH)

( * ) Notice: Subject to any disclaimer, the term of this patent is extended or adjusted under 35 U.S.C. 154(b) by 116 days.

(21) Appl. No.: 12/568,076

(22) Filed: Sep. 28, 2009

(65) Prior Publication Data

US 2011/0075806 A1    Mar. 31, 2011

(51) Int. Cl.
*A61N 5/10* (2006.01)

(52) U.S. Cl. .......................................................... 378/65
(58) Field of Classification Search .................... 378/64, 378/65, 69
See application file for complete search history.

*Primary Examiner* — Jurie Yun
(74) *Attorney, Agent, or Firm* — Peter Su; SNR Denton US LLP

(57) ABSTRACT

Systems and methods for providing radiosurgery treatment to a patient by combining methods from both traditional radiosurgery and radiotherapy are disclosed. A dose sufficient to kill tissue is applied to a target area while a steep drop off, or gradient, is provided at the border between the target area and adjacent areas so that other portions of the brain or nearby structures or organs are not damaged. The treatment plan is optimized by using both measures known in the art along with a new gradient index or curve that indicates the amount of the drop off at the border between the target area and the surrounding tissues.

23 Claims, 5 Drawing Sheets

TREATMENT PLAN OPTIMIZATION METHOD FOR RADIOSURGERY

FIELD OF THE INVENTION

The present invention relates to radiosurgery. More specifically, the invention relates to a method and apparatus for planning and performing radiosurgery on a subject that provides a desired three-dimensional distribution of radiation dose to a target volume while minimizing the delivery of radiation to tissue that is directly adjacent to the target volume.

BACKGROUND OF THE INVENTION

Stereotactic radiosurgery (SRS) has been traditionally used to treat brain disorders such as brain tumors and lesions with a precise delivery of a high dose of radiation. Focused radiation beams are delivered to a specific area of the brain, in essence burning tissue to treat abnormalities, tumors or functional disorders. The radiation is often applied in a single dose during a one-day session. Single-session radiosurgery normally has such a dramatic effect in the target zone that it is as if the tissue were removed, and thus the changes are considered "surgical."

Radiosurgery historically began by treating targets in the head and neck, because these areas can be immobilized with a skeletal fixation device that completely restricts the head's movement, permitting the most precise and accurate treatment. One-session treatments without such a skeletal fixation device have not been recommended because of the high potential for damage to healthy brain tissue, cranial nerves (optic, hearing, etc.) and the brain stem.

The clinical targets for radiosurgery are generally relatively small and well defined. High-resolution 3D imaging techniques such as CT and MRI help identify and clinically define these targets and the critical structures surrounding them. Through the use of three-dimensional computer-aided planning and the high degree of immobilization, stereotactic radiosurgery attempts to minimize the amount of radiation that passes through healthy brain tissue. This may be the primary treatment, used for example when a tumor is inaccessible by surgical means, or as a boost or adjunct to other treatments for a recurring or malignant tumor, although in some cases, radiosurgery may be inappropriate.

Stereotactic radiosurgery plans are often done using cone arcs, a well established technique in which open-ended metal cones are placed over one or more radiation sources. Cone arcs result in ball-shaped regions of high intensity radiation near isocenters that provide sharp dose gradients around target regions. For this reason, cone arc therapy is well suited for circular or spherical regions, but more difficult to use for irregular areas.

However, cone arc therapy is generally done mostly manually, relying on the skill of the user, i.e., the radiosurgeon. While a radiation source may be moved in an arc to match the outline of the target region, the user adjusts the isocenters manually. There is generally no shaping of the radiation beam other than to create the circular isocenters, and thus with limited exceptions there are no other shapes such as might be created using a leaf shutter as in radiation therapy. It is believed that there is also no dose distribution-based optimization of the radiation, other than adjusting the size of the isocenters.

While trajectory and arc treatments with multi-leaf collimators have proven efficient and practical in other fields of radiation therapy they are not yet widely used in radiosurgery.

Thus, optimization methods that are specially designed to meet radiosurgery needs have not been available for intensity modulated trajectory and arc treatments. For example, in complex cases the treatments may require more isocenters, while a low number of isocenters is preferred due to shorter treatment times.

Fractionated stereotactic radiation treatments, in which the radiation dose is received over a period of days or weeks, are sometimes used with the assistance of removable masks and frames. These devices generally achieve a lesser degree of immobilization than those used in single-session radiosurgery, and thus increase the risk of unintentionally exposing healthy tissue to radiation. Thus, as with single session radiosurgery, body radiosurgery using fractionated treatments is rare, as it is difficult to adequately immobilize and treat the body, although such treatment is becoming more common, particularly for targets in the spine and other extracranial organs. Recent studies have also suggested that this strategy can be more effective at killing or controlling certain types of cancer.

By contrast, external beam radiotherapy, often simply referred to as radiotherapy, is a radiation delivery procedure that generally uses a number of dose fractions, as many as 30 or more, of low dose high-energy radiation. Radiotherapy is usually administered over a period of weeks, and is typically used for larger tumors, a larger number of tumors, for end-stage disease tumors in combination with chemotherapy, and for systemic diseases such as blood-borne cancers. The goal of radiotherapy is tumor control or disease palliation; it is sometimes said to operate under the radiobiological assumptions of the "Four Rs," reoxygenation, reassortment, repopulation, and repair.

In radiotherapy, the goal is typically different than that in radiosurgery; rather than a dose sufficient to kill all tissue in the target area, radio therapy seeks to obtain a flat, homogenous and continuous dose across the target area, with a low dose in the surrounding areas. This is typically accomplished by intensity modulated treatments which optimize the radiation from different directions, often with the use of a leaf shutter on the radiation source that may be adjusted so that a different shape or cross-section is projected onto the patient from each direction where the radiation source is activated.

In other prior art methods dose-volume histogram (DVH) objectives, monitor unit (MU) objectives and normal tissue objectives have been used to optimize intensity modulated trajectory treatments. It is believed that DVH data has even been occasionally used with leaf shutters in radiosurgery. But DVH data has no spatial data, making it more complex to get plans that meet the necessary objectives typical for radiosurgery treatments.

For these and other reasons, techniques used in radiosurgery are generally not used in radio therapy, and vice versa. It would be useful to have an intensity modulated trajectory and arc optimization method that allows efficient optimization of properties that are important in radiosurgery applications.

SUMMARY OF THE INVENTION

The present invention relates to a method and apparatus for planning and performing radiosurgery on a subject that provides a desired three-dimensional distribution of radiation dose to a target volume while minimizing the delivery of radiation to tissue that is directly adjacent to the target volume. Methods from both traditional radiosurgery and radiotherapy are combined, allowing a dose sufficient to kill tissue to be applied to a target area with a steep drop off, or gradient, in adjacent areas so that other areas of the brain or nearby critical structures are not damaged. The treatment plan is optimized by using both measures well known in the field as well as a new gradient index or curve that indicates the amount of the drop off at the border between the target area and the surrounding tissues.

In one embodiment of the invention a method for planning delivery of a radiation dose to a target area within a subject comprises the steps of defining a desired dose distribution to be delivered to the target area; defining a gradient index at the border of the target area which indicates a desired reduction in dose from the target area to the surrounding tissue; specifying an initial plurality of beam aperture positions points along a trajectory which involves relative movement between a radiation source and the subject; and iteratively optimizing a simulated dose distribution relative to the desired dose distribution and the gradient index to determine one or more radiation delivery parameters associated with each of the initial plurality of beam aperture positions.

In another embodiment of the invention, a radiation treatment system comprises a beam source configured to generate a beam of radiation; a gantry configured to move the beam source; and a computing device configured to receive a definition of a target area, a desired dose to the target area, and a gradient index at the border of the target area which indicates a desired reduction in dose from the target area to the surrounding tissue, specify a plurality of initial beam aperture positions points along a trajectory which involves relative movement between a radiation source and the subject, and iteratively optimize a simulated dose distribution relative to the desired dose distribution and the gradient index to determine one or more radiation delivery parameters associated with each of the plurality of beam aperture positions.

In still another embodiment of the invention, a computing system comprises an input means for receiving a definition of a target area, a desired dose to the target area, and a gradient index at the border of the target area which indicates a desired reduction in dose from the target area to the surrounding tissue; an aperture position engine for selecting a plurality of initial beam aperture positions points along a trajectory which involves relative movement between a radiation source and the subject; and an optimization engine for iteratively optimizing a simulated dose distribution relative to the desired dose distribution and the gradient index to determine one or more radiation delivery parameters associated with each of the plurality of beam aperture positions.

DETAILED DESCRIPTION OF THE INVENTION

The invention includes systems and methods for providing radiosurgery treatment to a patient by combining methods from both traditional radiosurgery and radiotherapy so that a dose sufficient to kill the targeted tissue is applied while allowing a steep drop off, or gradient, in adjacent areas so that other areas of the brain or nearby structures such as the optic nerve are not damaged. The treatment plan is optimized by using both measures known in the art along with a new gradient index or curve that indicates the amount of the drop off at the border between the target area and the surrounding tissues.

Systems and methods using the present invention will include, for example, a beam source configured to provide a beam of therapeutic radiation. The beam of radiation is shaped by, for example, a multi-leaf collimator on an aperture that is moved, e.g., rotated, around a treatment volume in the patient using a gantry. The treatment volume typically includes a tumor or other part of the patient head or neck area that is to be subjected to radiosurgery.

Some embodiments further include a computing device configured to determine both the optimum positions in the rotation around the patient for exposure with the aperture, the optimal intensity of the radiation beam at each position, and the best positions for the leaves within the collimator at each position. The optimum aperture and leaf positions and beam intensity are iteratively determined from an initial estimate to provide the desired high dose to the target area and the desired steep drop off to the surrounding areas.

Figure 1:
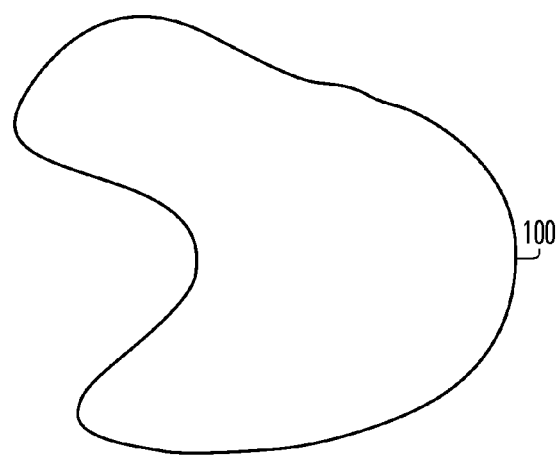
FIG. 1 illustrates a cross-section of an exemplary treatment volume.

FIG. 1 illustrates a cross-section of an exemplary Treatment Volume 100. This cross-section may be projected to an aperture along the direction of a radiation beam. As the position of the aperture changes, the projection of the projected cross-section is also likely to change according to the three-dimensional shape of Treatment Volume 100. Treatment Volume 100 may include, for example, a tumor or other area of brain or neck tissue that requires radiosurgical "removal."

Using traditional cone arc techniques, an irregular shape such as Treatment Volume 100 is treated by approximating the shape as a plurality of balls each small enough to fit into Treatment Volume 100. Each of the balls corresponds to a single isocenter, so that Treatment Volume 100 is irradiated multiple times with overlapping isocenters. This is not only inefficient, but there may also be undesired interactions between the isocenters. Note that the shape of Treatment Volume 100 shown in FIG. 1 is an arbitrary shape used for illustrative purposes; Treatment Volume 100 may take a wide variety of different shapes and, thus, result in a wide variety of cross-sections. Also, as above, trajectory treatments are generally not used with cone arc therapy.

Certain dose distribution measures are commonly used with cone arc therapy. These include the Coverage Index, Homogeneity Index, and Conformity Index. The Coverage Index uses isodose lines (contours of equal dose) to determine whether the entire subject area has received an adequate dose. If the isodose line corresponding to 90% of the prescribed dose completely encloses the target area, the plan is considered to follow the treatment protocol. If the 90% isodose line does not completely enclose the target but an 80% isodose line does so, the treatment is considered to be a minor deviation from the plan. Any other variation is a major deviation.

The Homogeneity Index is the ratio of the maximum dose to the prescribed dose. If it is less than 2 times the prescribed does, the plan is considered to follow the treatment protocol. If the Homogeneity Index is between 2 and 2.5, the treatment is considered to be a minor deviation from the plan, and if it is greater than 2.5 it is a major deviation from the desired treatment.

The Conformity Index is the ratio of the prescription isodose volume to the target volume (calculated from the integral dose volume histograms for the target volume and the normal tissue volume). If the ratio is between 1 and 2, the plan is per protocol. If it is between 2 and 2.5, it is a minor deviation, and greater than 2.5, a major deviation from the treatment plan.

However, unlike the present invention, these measures are not optimized, are not used with intensity modulated trajectory treatments, and are not used with leaf collimators. Rather, as above, the cone arcs are generally adjusted manually until these indices are at least within the ranges considered minor deviations from the treatment plan. Further, these measures do not give a full view of what is happening at the border between the target area and the surrounding tissues.

For this reason, the present invention adds a Gradient Index and curve shape to allow more visibility and control of the dose in the vicinity of the border when the target area is close to a specific critical organ or tissue. It is generally preferable to have as steep a gradient as possible between the target area and any critical tissue. As will be seen in FIG. 4 below, the Gradient Index may be visualized as a graph of dose on one axis and distance from the border on the other. For simplicity, only regions inside the target area and critical tissues are included, and only the worst dose at each distance is shown (lowest dose in target and highest dose in critical tissue).

In general, a method according to the present invention has the following steps. First, a user, such as a radiosurgeon, defines the two regions of interest and the boundary between them, one region being the tumor or other area, for example in the head or neck of the patient, that is to be treated, and the other region being any critical organs or regions in which it is desired to keep the radiation below some critical level at which the organs or regions will be damaged. The desired minimum dose for the target region and maximum dose for the critical region are specified, thus determining the desired Gradient Index. The user may add direction dependence to the objective, i.e., indicate that the Gradient Index need only apply in one direction or should be different in different directions from the tumor. For example, there may be a critical organ on only one side of tumor and not another. A distance map is created for each point in the tumor and organ which indicates each point's distance from the boundary.

Next, a starting treatment plan is selected, in which a plurality of points for exposure from the radiation aperture are selected along a trajectory around the target area and an intensity and shape of the radiation beam are selected for each point. Using this treatment plan, the resulting dose at each point in the target area and surrounding region is calculated. The dose distribution resulting from the treatment plan is then examined, and particularly evaluated for the resulting dose at each distance from the border. The results may be plotted as described above and shown in FIG. 4.

The treatment plan is then iteratively altered by, for example, adjusting the intensity or shape of the radiation beam at each the aperture points along the trajectory. Exposure points may also be added to or removed from the trajectory, and/or the trajectory itself may be altered. The dose distribution is reevaluated after each alteration until the resulting dose distribution meets the desired exposure criteria.

Figure 2:
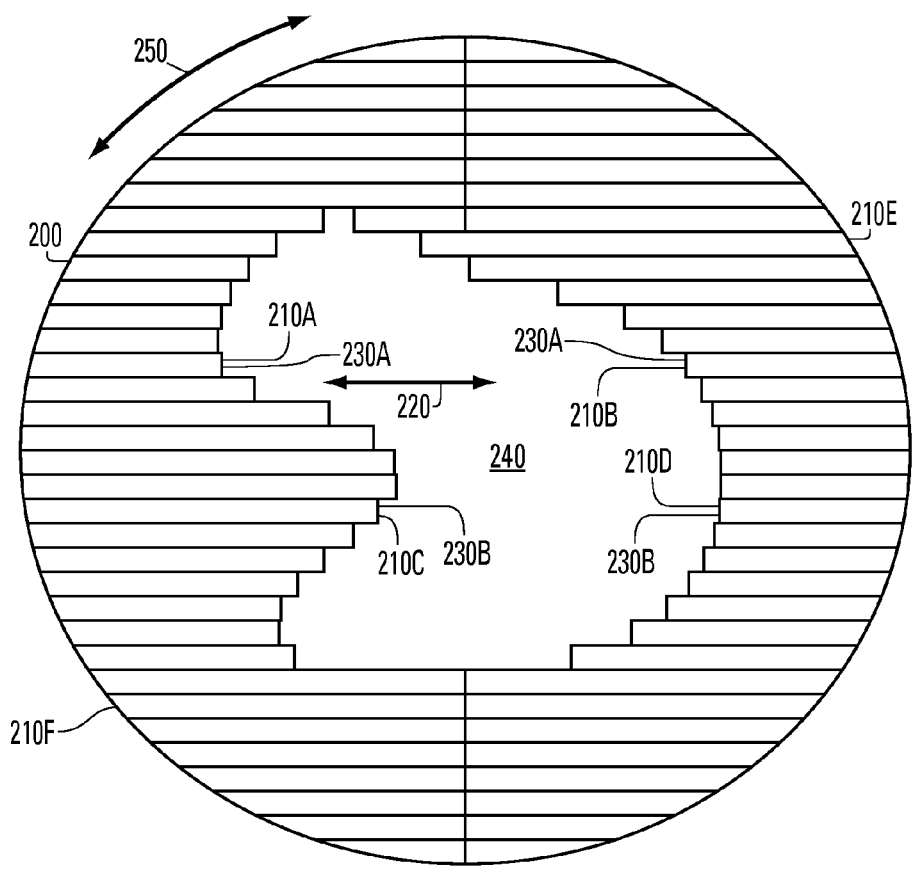
FIG. 2 illustrates an aperture configured to shape a radiation beam to match the treatment volume illustrated in FIG. 1, according to various embodiments of the invention.

A typical environment in which the present invention may be used is now described. FIG. 2 illustrates an Aperture 200 configured to shape a radiation beam to match Treatment Volume 100 illustrated in FIG. 1, according to various embodiments of the invention. Aperture 200 includes a plurality of movable Leaves 210, some of which are individually designated 210A-210F. Each of Leaves 210 typically includes a plate having a thickness in the direction parallel to the radiation beam (perpendicular to the image of FIG. 2) that is sufficient to greatly attenuate that part of the radiation beam that is blocked by one of Leaves 210. Opposing members of Leaves 210 are referred to as Leaf Pairs 230. For example, Leaves 210A and 210B comprise a Leaf Pair 230A. Likewise, Leaves 210C and 210D comprise a Leaf Pair 230B.

Leaves 210 may be moved in Directions 220 in order to provide one or more Opening 240. For example, in FIG. 2 Leaf Pair 230A is disposed to match the projection of Treatment Volume 100 along the direction of the radiation beam to Aperture 200. Opening 240 may include a single opening as illustrated in FIG. 2, or a plurality of separate openings. In some embodiments, Aperture 200 can be rotated within the plane of the figure, e.g., in Directions 250.

Figure 3:
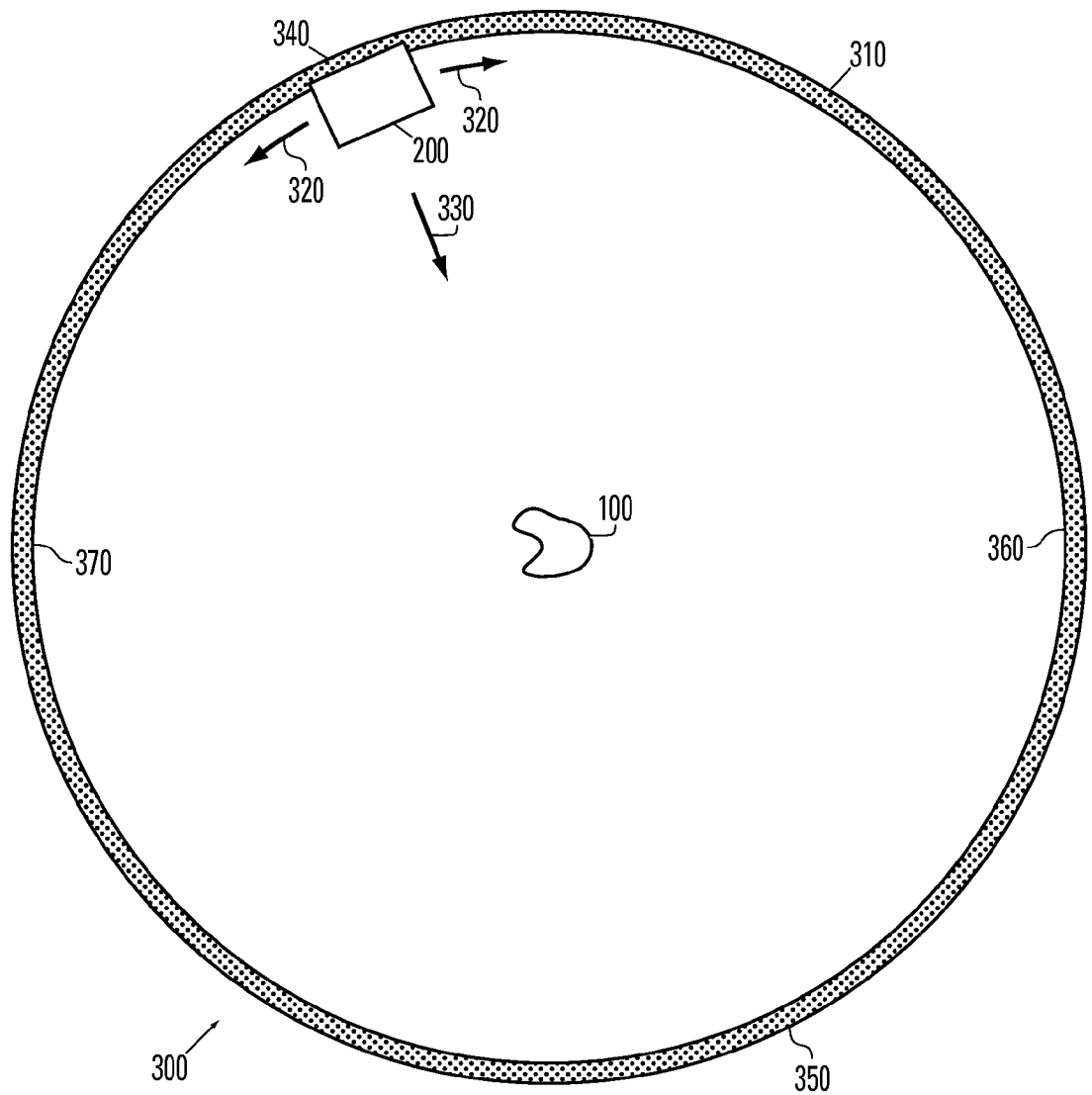
FIG. 3 illustrates a radiation treatment system including a 360 degree gantry configured to support and move the aperture of FIG. 2, according to various embodiments of the invention.

FIG. 3 illustrates a Radiation Treatment System, generally designated 300 and including a Gantry 310 that can move 360 degrees around the patient and is configured to support and move Aperture 200 of FIG. 2. Gantry 310 is configured to move Aperture 200 and optionally part of a beam source (not shown) in directions 320. As Aperture 200 is moved around Treatment Volume 100, the beam of radiation arrives at Treatment Volume 100 from a variety of directions. For example, at the position of Aperture 200 illustrated in FIG. 3, a radiation beam is directed in a Direction 330.

As Aperture 200 is moved around Treatment Volume 100, the projection of Treatment Volume 100 onto Aperture 200 changes according to the three-dimensional shape of the Treatment Volume 100. As is further described herein, this changing projection is one of the factors that may be used to determine a position for leaves 210. The projection of Treatment Volume 100 will be approximately the same when Aperture 200 is positioned in opposing positions around Gantry 310. For example, the projections from a Position 340 and a Position 350 will be approximately the same. For the purposes of this discussion, these positions are referred to herein as the 11:00 and 5:00 positions respectively. Likewise, a Position 360 and a Position 370 are referred to herein as the 3:00 and 9:00 positions respectively. Other positions may be referred to herein using similar clock based references.

Figure 4:
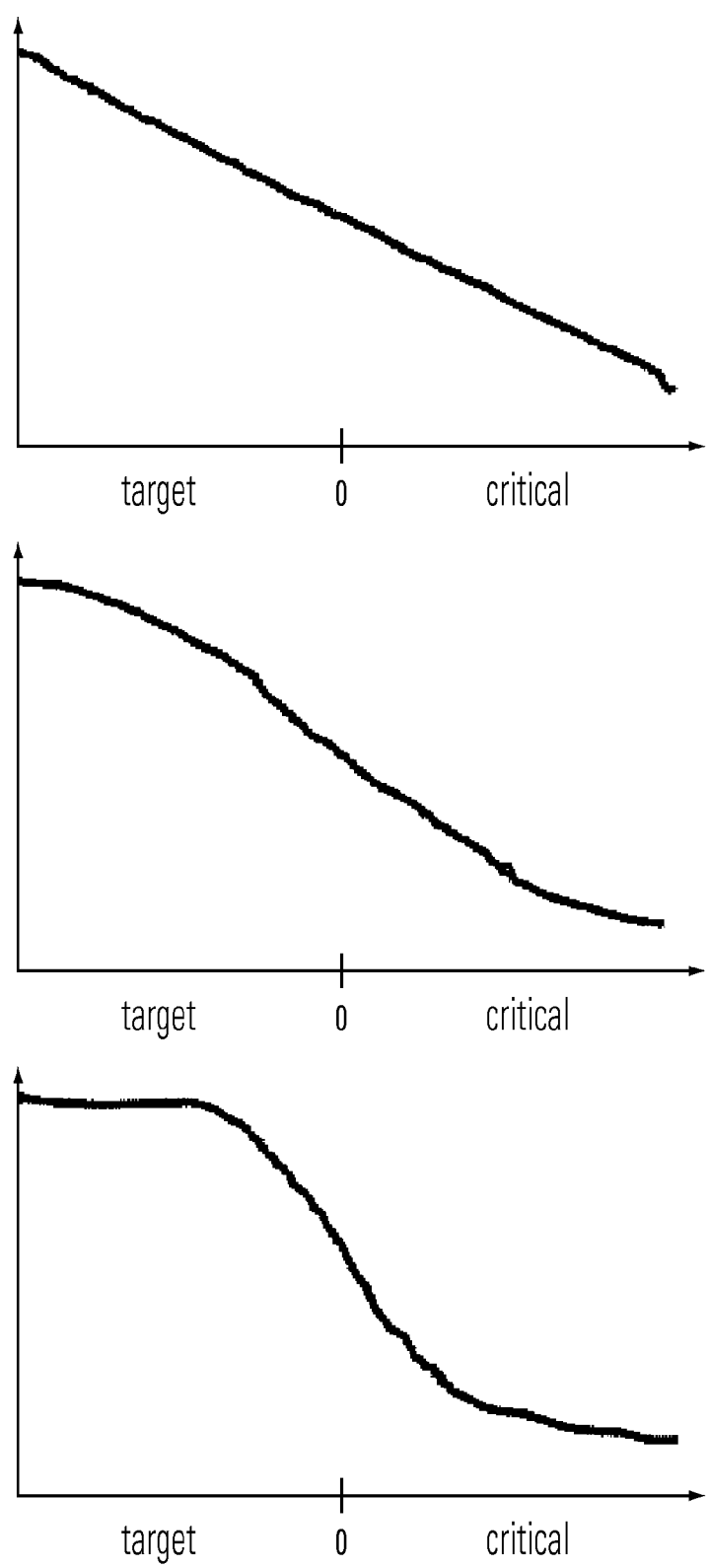
FIG. 4 is an illustration of a gradient index and its improvement through optimization of the radiation profile.

FIG. 4 shows how a Gradient Index curve may be optimized in the present invention. The top graph shows how the dose, shown on the vertical axis, might be expected to vary with the distance from the border between the targeted area and the critical tissue as shown on the horizontal axis, with 0 the border and "target" indicating increasing distance into the area to be treated to the left and "critical" increasing distance into the surrounding area to the right, under an initial proposed treatment plan. The proposed treatment plan includes a plurality of suggested positions in the rotation around the patient from which the patient is to be irradiated, the intensity of the radiation beam at each position, and the positions for the leaves within the collimator at each position.

As this curve is clearly not optimal, the parameters are varied by changing the positions on the trajectory from which radiation is to be delivered, the intensity at one or more of those positions, and/or the positions of the leaves at one or more positions. The iterations continue until optimum aperture and leaf positions and beam intensity are determined that provide the desired high dose to the target area and the desired steep drop off to the surrounding areas.

The user (radiosurgeon) may place objectives on the shape of the curve, such as those used in the conventional indices described above. For example, it might be specified that regions more than 5 mm inside the target area must receive more than 90% of the prescribed dose, or that regions more than 5 mm inside any critical organ must receive less than 30% of the prescribed dose. The gradient information may also be reduced to a single number. For example, a sigmoid function such as $$\text{Dose}(x)=1/(1+\exp(-tx))$$

where x is the distance from the border, may be used as the dose curve with the t value shown to the user. Alternatively, the user could also set constraints on t or an optimizer (described below) could have an objective to maximize t.

Figure 5:
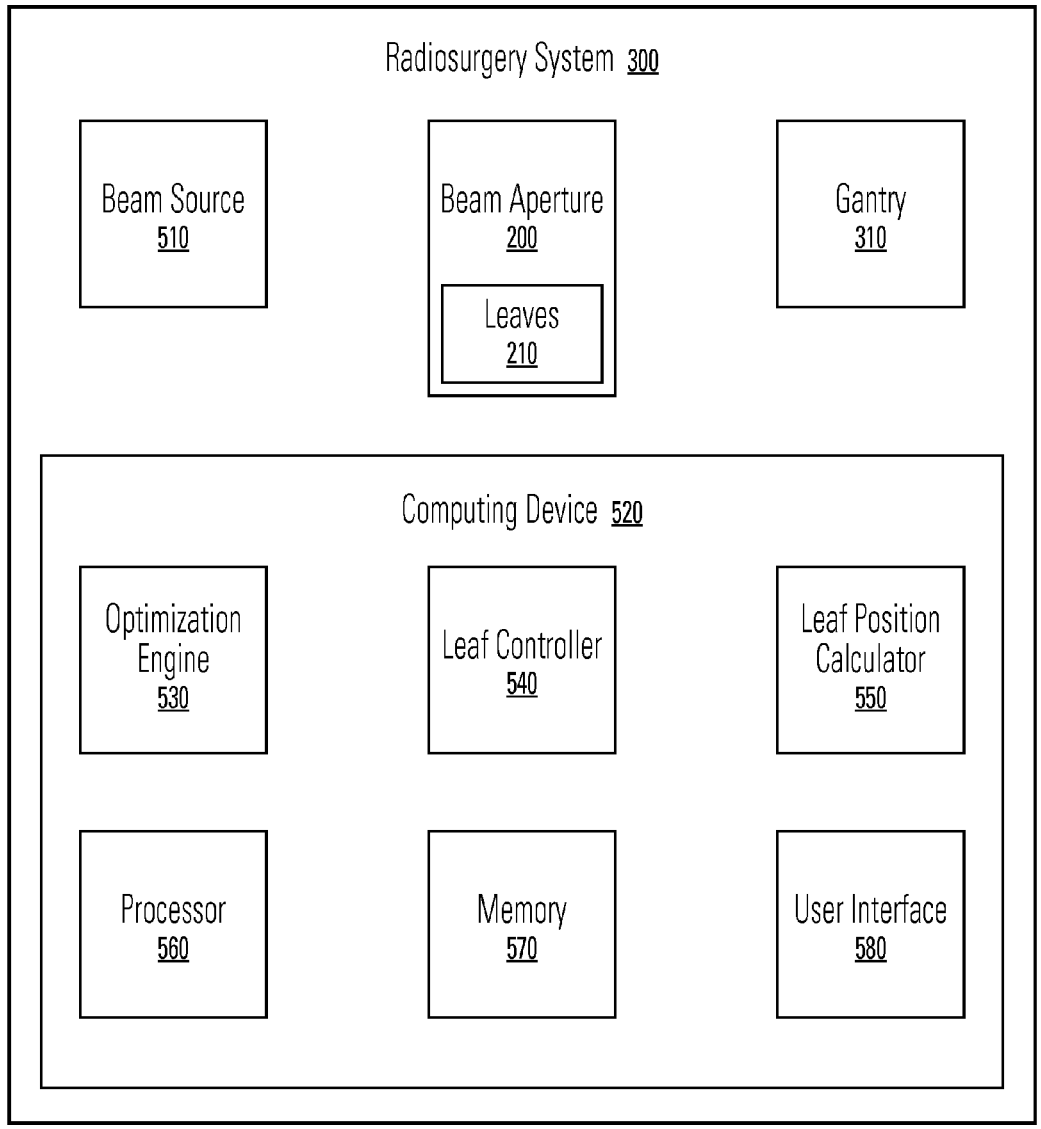
FIG. 5 is a block diagram of a radiation treatment system, according to various embodiments of the invention.

FIG. 5 is a block diagram of Radiation Treatment System 300 of FIG. 3, which includes a Beam Source 510, Beam Aperture 200 as above and Gantry 310 as above. Beam Source 510 is configured to generate a beam of therapeutic radiation. This beam of radiation may include x-rays, particles, and/or the like. For example, in some embodiments, Beam Source 510 includes an x-ray source. In some embodiments, Beam Source 510 includes a particle beam source such as a particle accelerator. Beam Source 510 is optionally configured for generating imaging radiation as well as therapeutic radiation.

Radiation Treatment System 300 further includes a Computing Device 520 configured to optimize the radiosurgery plan using an Optimization Engine 530, to send signals to Beam Aperture 200 to position Leaves 210 using a Leaf Controller 540, and to calculate leaf positions using a Leaf Position Calculator 550. Computing Device 520 typically further comprises a Processor 560 and Memory 570.

Processor 560 is configured to execute computing instructions in order to perform methods and functions described herein. These computing instructions may be embodied in hardware, firmware, and/or software. Memory 570 is configured to store the computing and optimization instructions, data related to the three-dimensional dose distribution, data related to the radiation beam, data defining the treatment zone, calculated leaf positions, and/or the like. Computing Device 520 may further include a User Interface 580. User Interface 580 may include a display and/or a graphical user interface, and is configured for a user to control Radiation Treatment System 300, designate the desired Gradient Index or other indices as above, designate a treatment volume, and/or the like.

Optimization Engine 530 is configured for optimizing the treatment plan to obtain appropriate aperture and leaf positions and beam intensity for achieving the desired three-dimensional dose distribution within a treatment volume and desired Gradient Index. In some embodiments, Optimization Engine 530 is configured to receive specifications for a desired three-dimensional dose distribution from a user via User Interface 480. The spatial characteristics of the desired three-dimensional dose distribution may be designated manually by having the user mark boundaries of the spatial distribution on an image of Treatment Volume 100, with the desired Gradient Index also provided. Alternatively, the spatial distribution may be automatically designated by applying a filter to an image of Treatment Volume 100, such as selecting image pixels within a certain intensity range. A combination of these manual and automated approaches may also be used. As above, the Gradient Index is selected to avoid delivering radiation to healthy radiation sensitive organs.

Referring again to FIG. 5, Leaf Controller 540 is configured to send control signals to Beam Aperture 200 so as to move Leaves 210 to the leaf positions calculated using Leaf Position Calculator 550. In some embodiments, these control signals include digital data to be delivered to Beam Aperture 200. Leaf Controller 540 may include computing instructions and/or hardware configured for communication and signal processing. Leaf Position Calculator 550 is configured to calculate positions for each Leaf 210 at each position of Gantry 310. These leaf positions are calculated so as to achieve the desired three-dimensional dose to the target area and Gradient Index and are selected using Optimization Engine 530.

Typically, Optimization Engine 530 starts the optimization process by accepting the definition of the target area and the surrounding critical area and the boundary between them, and the initial proposed treatment plan. A distance map is created for each point in the tumor and organ which indicates each point's distance from the boundary.

The initial treatment plan typically contains a plurality of points for exposure from the radiation aperture selected along a trajectory around the target area and an intensity and shape of the radiation beam are selected for each point. The Optimization Engine 530 uses the proposed treatment plan to calculate the resulting dose at each point in the target area and surrounding region. The dose distribution resulting from the treatment plan is then examined, and particularly evaluated for the resulting dose at each distance from the border using the distance map. The results may be plotted as described above and shown in FIG. 4.

The treatment plan is then iteratively altered by, for example, adjusting the intensity or shape of the radiation beam at each the aperture points along the trajectory. Exposure points may also be added to or removed from the trajectory. The dose distribution is reevaluated after each alteration until the resulting dose distribution meets the desired exposure criteria.

In some embodiments, the iterations may begin randomly, i.e., a leaf is moved at one position of the aperture, or the beam intensity is altered at an aperture position, or the aperture position itself is changed slightly. If the Gradient index curve improves, another change is made. If the Gradient Index curve gets worse, the change is removed and another change is tried. In other embodiments, the user may wish to manually suggest changes, or to indicate priorities in the way changes are made. Such optimization techniques are known in the art, although not for radiosurgery and not with a Gradient Index.

In various embodiments, the Coverage Index, Homogeneity Index, and/or Conformity Index may be used as an optimization objective along with the Gradient Index or curve shape. Alternatively, any of these indices may be calculated from each proposed plan during optimization and shown to the user, who may then make changes in the desired treatment plan based on the results.

Other prior art techniques may be used with the present invention. For example, simulated annealing or back-projection techniques may be used. In such methods, the deviation from a desired dose is calculated at each position in the region of interest. The points are then "back-projected" to the radiation source or the plane of a beam-limiting device such as a collimator. Next, the difference values that project to same region in a plane (for example a pixel in 2D map) in the radiation source or beam limiting device are summed to produce a map of how the radiation from that plane should be changed to produce a dose distribution that more closely matches the desired one. The treatment plan (which could be a set of beam intensities or a group of machine parameters) are changed according to the projected map. This process is then iterated as many times as necessary to obtain the desired treatment plan.

Figure 6:
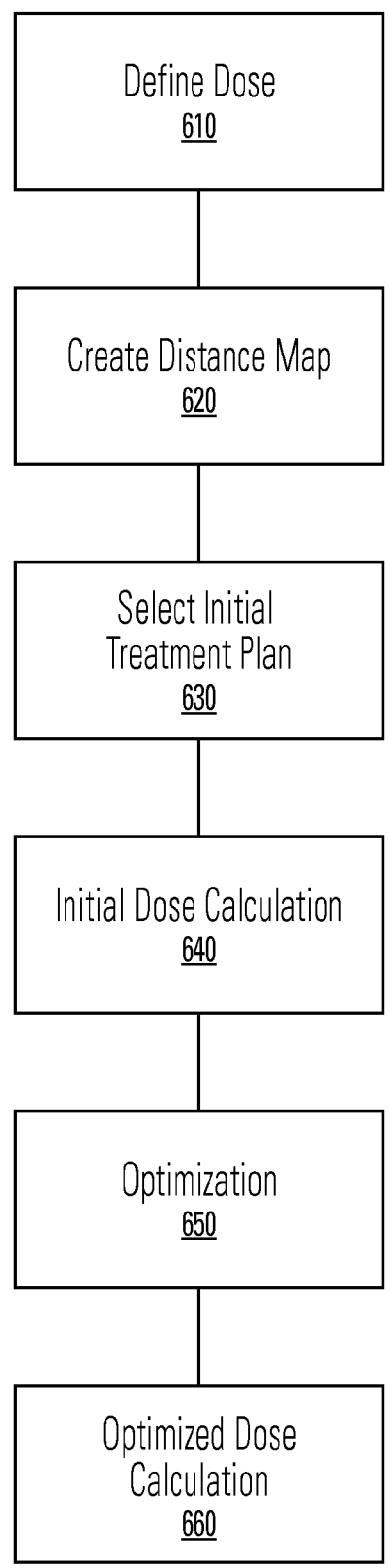
FIG. 6 is a flowchart of a radiosurgical method of providing radiation to a treatment volume, according to various embodiments of the invention.

FIG. 6 illustrates a method of preparing a radiosurgery plan for a treatment volume, such as Treatment Volume 100, according to various embodiment of the invention. In these methods, target and critical areas and desired treatment doses and Gradient Index are defined, an initial proposed treatment plan is specified, a distance map is created, and the treatment plan is iteratively modified until the stated criteria are met.

In a Define Dose Step 610, a user, such as a radiosurgeon, defines the two regions of interest and the boundary between them, the dose desired to be applied to the target area, and the maximum dose desired for the adjacent critical area. The characteristics of the desired three-dimensional dose distribution have been specified by a user, e.g., by a medical doctor, by a physicist or by a dosimetrist, based on medical needs. The values of the desired three-dimensional dose distribution may vary as a function of position within the Treatment Volume 100.

At Distance Map step 620, a distance map is created for each point in the tumor and organ which indicates each point's distance from the boundary.

Next, at Select Initial Treatment Plan 630, an initial treatment plan is selected, in which a plurality of points for exposure from the radiation aperture are selected along a trajectory around the target area and an intensity and shape of the radiation beam are selected for each point.

Using this initial treatment plan, the resulting dose at each point in the target area and surrounding region is calculated at Initial Dose Calculation step 640. The dose distribution resulting from the treatment plan is then examined, and particularly evaluated for the resulting dose at each distance from the border. The results may be plotted as described above and shown in FIG. 4.

In Optimization step 650, the treatment plan is then iteratively altered by, for example, adjusting the intensity or shape of the radiation beam at each the aperture points along the trajectory. Exposure points may also be added to or removed from the trajectory. The dose distribution is reevaluated after each alteration until the resulting dose distribution meets the desired exposure criteria.

At Optimized Dose Calculation step 660, the optimized treatment plan is evaluated. If the optimized plan produces the desired dose, including the desired Gradient Index, i.e., the desired reduced dose to the critical area surrounding the target area, the plan is accepted. If the optimized plan does not produce the desired dose, Optimization step 650 may be repeated until the desired dose is obtained.

Several embodiments are specifically illustrated and/or described herein. However, it will be appreciated that modifications and variations are covered by the above teachings and within the scope of the appended claims without departing from the spirit and intended scope thereof. For example, while many of the illustrations and examples disclosed herein are in a two-dimensional context, one of ordinary skill in the art will understand that these same illustrations and examples are intended to be applied to the three dimensions actually encountered in radiation therapy. Further, various embodiments of the invention include computing instructions configured to perform various methods and functions described herein, and stored on a computer readable media for use on a general purpose computer attached to a radiation delivery device. Some embodiments of the invention do not include directly controlling a radiation delivery device. For example, the information produced using the methods discussed herein may be used as a starting point for other algorithms, or can be stored for later use. In these embodiments, Leaf Controller 540 is optional.

The embodiments discussed herein are illustrative of the present invention. As these embodiments of the present invention are described with reference to illustrations, various modifications or adaptations of the methods and or specific structures described may become apparent to those skilled in the art. All such modifications, adaptations, or variations that rely upon the teachings of the present invention, and through which these teachings have advanced the art, are considered to be within the spirit and scope of the present invention. Hence, these descriptions and drawings should not be considered in a limiting sense, as it is understood that the present invention is in no way limited to only the embodiments illustrated.

What is claimed is:

1. A method for planning delivery of a radiation dose to a target area within a subject, the method comprising:
    defining a desired dose distribution to be delivered to the target area;
    defining a gradient index at the border of the target area indicating a desired reduction in dose from the target area to the surrounding tissue;
    specifying a plurality of beam aperture points along a trajectory comprising relative movement between a radiation source and the subject; and
    iteratively optimizing a simulated dose distribution relative to the desired dose distribution and the gradient index to determine one or more radiation delivery parameters associated with each of the plurality of beam aperture points.

2. The method of claim 1, further comprising adding a second plurality of beam aperture points along the trajectory.

3. The method of claim 1, wherein iteratively optimizing a simulated dose distribution relative to the desired dose distribution and the gradient index further comprises iteratively optimizing the simulated dose distribution subject to one or more constraints.

4. The method of claim 1, wherein iteratively optimizing the simulated dose distribution to determining one or more radiation delivery parameters associated with each of the plurality of beam aperture points comprises, for each iteration:
    varying one or more of the radiation delivery parameters associated with one or more of the plurality of beam aperture points;
    determining a revised simulated dose distribution based on the one or more varied radiation delivery parameters;
    determining to accept or reject the one or more varied radiation delivery parameters by using an optimization algorithm and the revised simulated dose distribution; and
    updating the current radiation delivery parameters to include the one or more varied radiation delivery parameters if the one or more varied radiation delivery parameters is accepted.

5. The method of claim 1, wherein the one or more radiation delivery parameters comprise one or more beam-shaping parameters.

6. The method of claim 5, wherein the one or more beam-shaping parameters comprise one or more configurations of a multi-leaf collimator.

7. The method of claim 6, wherein iteratively optimizing a simulated dose distribution relative to the desired dose distribution and the gradient index further comprises calculating leaf positions for each leaf pair of the multi-leaf collimator in order to achieve the determined radiation delivery parameter associated with each of the plurality of beam aperture points.

8. The method of claim 7, further comprising using a leaf controller to move each leaf pair into the calculated leaf positions at each of the plurality of beam aperture points.

9. The method of claim 8, wherein calculating leaf positions further comprises determining that the calculated leaf positions can be achieved within the mechanical limitations of the multi-leaf collimator.

10. The method of claim 1, wherein the one or more radiation delivery parameters comprise a beam intensity.

11. The method of claim 1, wherein the one or more radiation delivery parameters comprise a position of the radiation source relative to the subject.

12. A radiation treatment system comprising:
a radiation source configured to generate a beam of radiation;
a gantry configured to move the radiation source; and
a computing device configured to:
receive a definition of a target area, a desired dose to the target area, and a gradient index at the border of the target area indicating a desired reduction in dose from the target area to the surrounding tissue;
specify a plurality of beam aperture points along a trajectory comprising relative movement between the radiation source and a subject; and
iteratively optimize a simulated dose distribution relative to a desired dose distribution and the gradient index to determine one or more radiation delivery parameters associated with each of the plurality of beam aperture points.

13. The radiation treatment system of claim 12, further comprising a beam aperture having a plurality of aperture leaves configured to shape the beam of radiation, and wherein the computing device is further configured to calculate a leaf position for each of the plurality of aperture leaves in order to achieve the determined radiation delivery parameter associated with each of the plurality of beam aperture points.

14. The radiation treatment system of claim 13, wherein the computing device is further configured to calculate a leaf position for each of the plurality of aperture leaves at each of the beam aperture points responsive to the desired dose distribution and gradient index thereby providing the desired dose distribution.

15. The radiation treatment system of claim 12, wherein the computing device is further configured to add a second plurality of beam aperture points along the trajectory.

16. The radiation treatment system of claim 12, wherein the computing device is further configured to iteratively optimize the simulated dose distribution relative to the desired dose distribution and the gradient index subject to one or more constraints.

17. The radiation treatment system of claim 12 wherein the computing device is further configured to iteratively optimize the simulated dose distribution to determine one or more radiation delivery parameters associated with each of the plurality of beam aperture points by, for each iteration:
varying one or more of the radiation delivery parameters associated with one or more of the plurality of beam aperture points;
determining a revised simulated dose distribution based on the one or more varied radiation delivery parameters;
determining, to accept or reject the one or more varied radiation delivery parameters by using an optimization algorithm and the revised simulated dose distribution; and
updating the current radiation delivery parameters to include the one or more varied radiation delivery parameters if the one or more varied radiation delivery parameters is accepted.

18. The radiation treatment system of claim 12, wherein the radiation source is an x-ray source.

19. A computing system comprising:
input means for receiving a definition of a target area, a desired dose to the target area, and a gradient index at the border of the target area indicating a desired reduction in dose from the target area to the surrounding tissue;
an aperture position engine for selecting a plurality of beam aperture points along a trajectory comprising relative movement between a radiation source and a subject; and
an optimization engine for iteratively optimizing a simulated dose distribution relative to a desired dose distribution and the gradient index to determine one or more radiation delivery parameters associated with each of the plurality of beam aperture points.

20. The computing system of claim 19, further comprising:
a leaf position calculator configured to calculate leaf positions for a plurality of leaves in a radiation beam aperture, the leaf positions being configured to achieve the determined radiation delivery parameter associated with each of the plurality of beam aperture points; and
a leaf controller configured to control the plurality of leaves according to the leaf positions calculated using the leaf position calculator.

21. The computing system of claim 19, wherein the optimization engine is further configured to instruct the aperture position engine to add additional beam aperture points along the trajectory.

22. The computing system of claim 19, wherein the optimization engine is further configured to iteratively optimize the simulated dose distribution subject to one or more constraints.

23. The computing system of claim 19, wherein the optimization engine is further configured to optimize the simulated dose distribution by, for each iteration:
varying one or more of the radiation delivery parameters associated with one or more of the plurality of beam aperture points;
determining a revised simulated dose distribution based on the one or more varied radiation delivery parameters;
determining to accept or reject the one or more varied radiation delivery parameters by using an optimization algorithm and the revised simulated dose distribution; and
updating the current radiation delivery parameters to include the one or more varied radiation delivery parameters if the one or more varied radiation delivery parameters is accepted.

* * * * *

UNITED STATES PATENT AND TRADEMARK OFFICE
CERTIFICATE OF CORRECTION

| | | |
|---|---|---|
| PATENT NO. | : 8,009,803 B2 | Page 1 of 1 |
| APPLICATION NO. | : 12/568076 | |
| DATED | : August 30, 2011 | |
| INVENTOR(S) | : Janne Ilmari Nord et al. | |

It is certified that error appears in the above-identified patent and that said Letters Patent is hereby corrected as shown below:

On the front page of the patent in the Title section:

• TREATMENT PLAN OPTIMIZATION METHOD FOR RADIOSURGERY should read
-- TREATMENT PLAN OPTIMIZATION METHOD FOR RADIOTHERAPY --.

Signed and Sealed this
Eighteenth Day of October, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,009,803 B2 | Page 1 of 1 |
| APPLICATION NO. | : 12/568076 | |
| DATED | : August 30, 2011 | |
| INVENTOR(S) | : Janne Ilmari Nord et al. | |

It is certified that error appears in the above-identified patent and that said Letters Patent is hereby corrected as shown below:

Title Page, Item (54) and at Column 1, lines 1 and 2, in the Title section:

• TREATMENT PLAN OPTIMIZATION METHOD FOR RADIOSURGERY should read
-- TREATMENT PLAN OPTIMIZATION METHOD FOR RADIOTHERAPY --.

This certificate supersedes the Certificate of Correction issued October 18, 2011.

Signed and Sealed this
Twenty-second Day of November, 2011

David J. Kappos
*Director of the United States Patent and Trademark Office*